United States Patent
Termanini

(10) Patent No.: US 10,463,543 B2
(45) Date of Patent: Nov. 5, 2019

(54) SELF-CURING ORTHOPEDIC SPLINT AND METHOD FOR APPLYING SAME

(71) Applicant: Zafer Termanini, Port Saint Lucie, FL (US)

(72) Inventor: Zafer Termanini, Port Saint Lucie, FL (US)

(73) Assignee: JOINT INNOVATION TECHNOLOGY, LLC, Boca Raton, FL (US)

( * ) Notice: Subject to any disclaimer, the term of this patent is extended or adjusted under 35 U.S.C. 154(b) by 0 days.

(21) Appl. No.: 15/866,464

(22) Filed: Jan. 10, 2018

(65) Prior Publication Data

US 2019/0209385 A1    Jul. 11, 2019

(51) Int. Cl.
*A61F 5/00*      (2006.01)
*A61F 13/04*     (2006.01)
*A61L 15/12*     (2006.01)
*A61L 15/14*     (2006.01)
*A61F 13/00*     (2006.01)

(52) U.S. Cl.
CPC .......... *A61F 13/041* (2013.01); *A61L 15/125* (2013.01); *A61L 15/14* (2013.01); *A61F 2013/00604* (2013.01); *A61F 2013/00625* (2013.01); *A61F 2013/00638* (2013.01); *A61F 2013/00817* (2013.01); *A61F 2013/00897* (2013.01)

(58) Field of Classification Search
CPC .............................. A61F 13/04; A61F 13/041
See application file for complete search history.

(56) References Cited

U.S. PATENT DOCUMENTS

| | | | | |
|---|---|---|---|---|
| 4,537,184 A | * | 8/1985 | Williams, Jr. | A61F 13/04 602/8 |
| 5,003,970 A | * | 4/1991 | Parker | A61F 13/04 206/389 |
| 5,284,468 A | * | 2/1994 | Nelson | A61F 5/05825 602/5 |
| 5,713,838 A | * | 2/1998 | Termanini | A61F 13/04 602/1 |
| 7,172,565 B2 | * | 2/2007 | Termanini | A61F 5/05825 602/5 |
| 2002/0161319 A1 | * | 10/2002 | Matsumoto | A61F 5/01 602/8 |
| 2010/0063431 A1 | * | 3/2010 | Bae | A61F 5/01 602/5 |

* cited by examiner

*Primary Examiner* — Kim M Lewis
(74) *Attorney, Agent, or Firm* — Norris McLaughlin, PA

(57) ABSTRACT

An orthopedic splint system comprising self curing splinting system that is applied to an injured limb without use of water. The splint material is contained in tear resistant outer pouch and an inner protective sleeve where a water-laden gel is contained in a pouch situated in direct contact with the splint material. The liquid pouch will be torn when a longitudinal tab, which is an integral part of the pouch, is pulled out releasing the water-laden gel which will come in contact with the splint system causing it to cure.

19 Claims, 4 Drawing Sheets

SELF-CURING ORTHOPEDIC SPLINT AND METHOD FOR APPLYING SAME

FIELD OF THE INVENTION

The present invention relates generally to the field of orthopedic medicine and more specifically to a novel orthopedic splints including a self curing waterless bandage adapted to be applied to an injured limb for purpose of immobilization, and water laden gel for purpose of curing the splint material.

BACKGROUND OF THE INVENTION

Conventionally, medical bandages and splints are used to immobilize broken bones. Generally, said splint are made of strips of plaster of Paris or fiberglass impregnated with water curable substance which hardens into a rigid structure once it makes contact with water. However, this procedure is cumbersome, messy and causes the splint to become wet. Furthermore, water may not be readily available in remote areas. Moreover, when the splint is applied to broken skin or an open wound, it represents a risk of infection since the water used to soak the material is non sterile.

SUMMARY OF THE INVENTION

The orthopedic splint system of this invention comprises a tear resistant outer bag and an inner envelop or protective sleeve containing a number of juxtaposed layers of orthopedic splint material impregnated with water curable resin commonly used in the orthopedic art. Said splint material can be fiberglass, polyester, nylon or plaster of Paris. Water or water-laden gel is supplied separately and packaged as an integral part of the self-curing splint system. Said water or water-laden gel liquid is supplied in a long pouch inserted between the layers of the splint. The liquid pouch having a portion at one end containing no liquid and forming an extension of the pouch.

The extension is split into three sections where the middle section is flipped over and laid over the pouch. The outer two sections are positioned toward the opposite end of the liquid pouch and will be used to anchor the liquid pouch to the protective pouch. The liquid pouch as described above is sandwiched between the layers of the splint material. The splint material and the liquid pouch are placed inside the protective pouch. Said protective pouch can be made out of non-woven material coated with a thin film of silicone or similar plastic material which render it air and moisture impermeable. The protective pouch is heat sealed all around except at a small area where the folded central extension tab of the liquid pouch passes through. The other two lateral extensions tabs at the opposite end of the liquid pouch are firmly attached by heat seal into the edge of the protective pouch. When manual traction is applied to the central slip tab it will cause the liquid pouch to rip and the fluid contained in the liquid pouch to be released and come in contact with the splint material.

The dry splint as described in this invention is suitable for use with any orthopedic casting material that is water-curable. The liquid pouch may contain water or viscous water-laden gel, commonly used in cosmetic or medical industry. The gel may also contain hardeners or accelerators that will interact with water curable resin such as tertiary amines, methylketones, copper tin salts used in appropriate percentages.

The dry splint system of the present invention provides a self-cured orthopedic splint material, which may consist of one or more layers of fiberglass or polyester sheets that are juxtaposed on top of each other. A liquid pouch containing water-laden gel and a protective pouch which is air and water tight. The liquid pouch is supplied with an extension tab at one end, which can be pulled through causing the rupture of the pouch and the release of the water-laden gel to interact with the resin contained in the splint material. In order to facilitate the curing process, the operator will have to spread and knead the splint in order to spread the released fluid. The resin will then cure causing the dry splint to become hard. The outer pouch of this splint system is a package that is formed of aluminum foil or plastic such as Mylar or alike. The outer pouch is resilient and tear resistant. It becomes obvious that the self cured splint of the present invention avoids the prior art inconvenience and shortcoming of removing the orthopedic casting material and dipping it in water before applying it onto the patient.

Among other significant advantages of the dry splint of this invention, is that the protective pouch is sprayed with antiseptic solution allowing the splint to be applied over an open wound or broken skin as frequently encountered in military battlefield, outdoors and vehicular accidents.

BRIEF DESCRIPTION OF THE DRAWINGS

A greater appreciation for the embodiment of the present invention will be gained by consideration of the figures in which.

DETAILED PRESCRIPTION OF THE INVENTION

Figure 1:
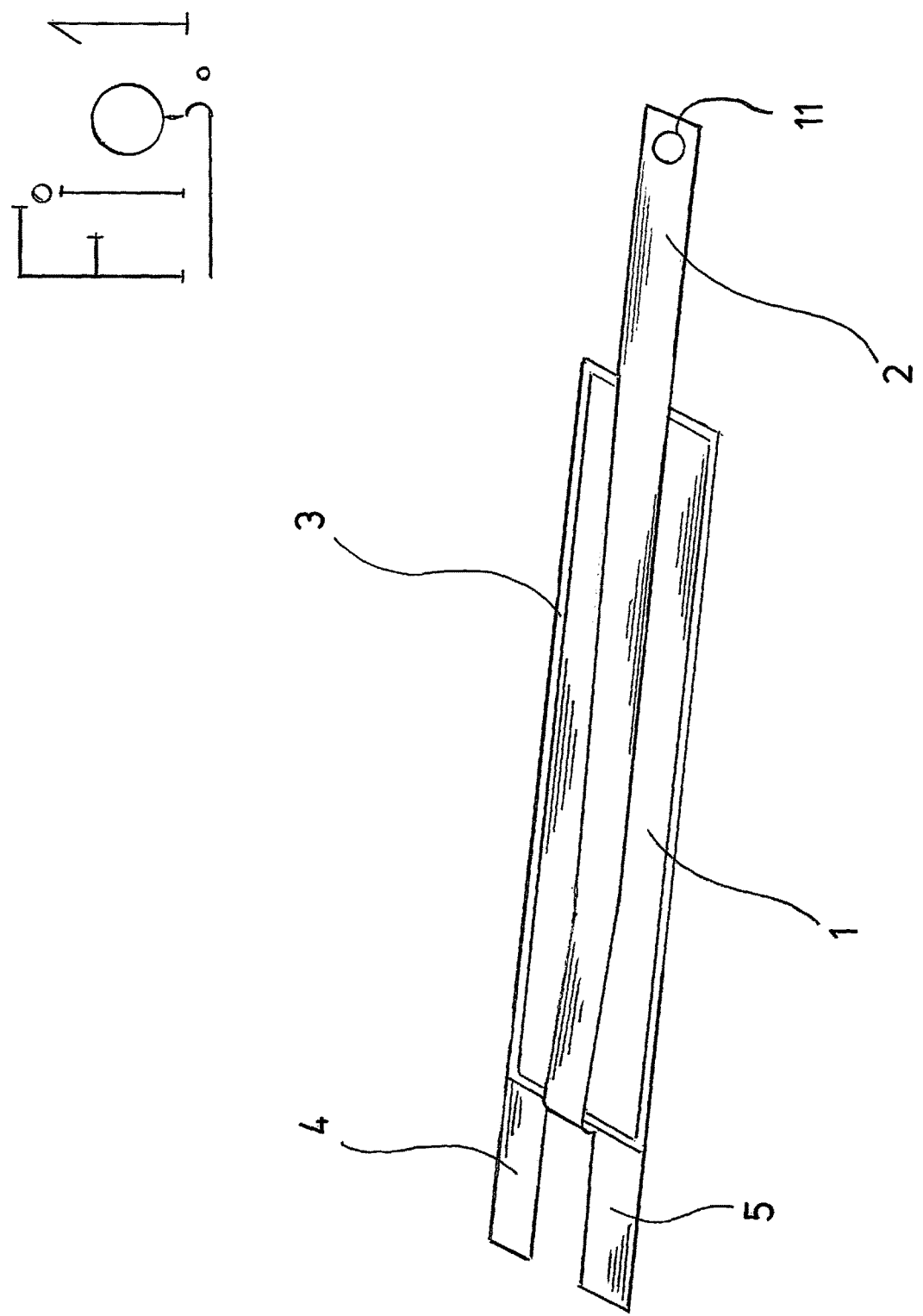
FIG. 1 is a perspective view of an embodiment of the invention showing the folded central portion to one end of the liquid pouch and the two side extensions to the opposite end of the liquid pouch.
Figure 2:
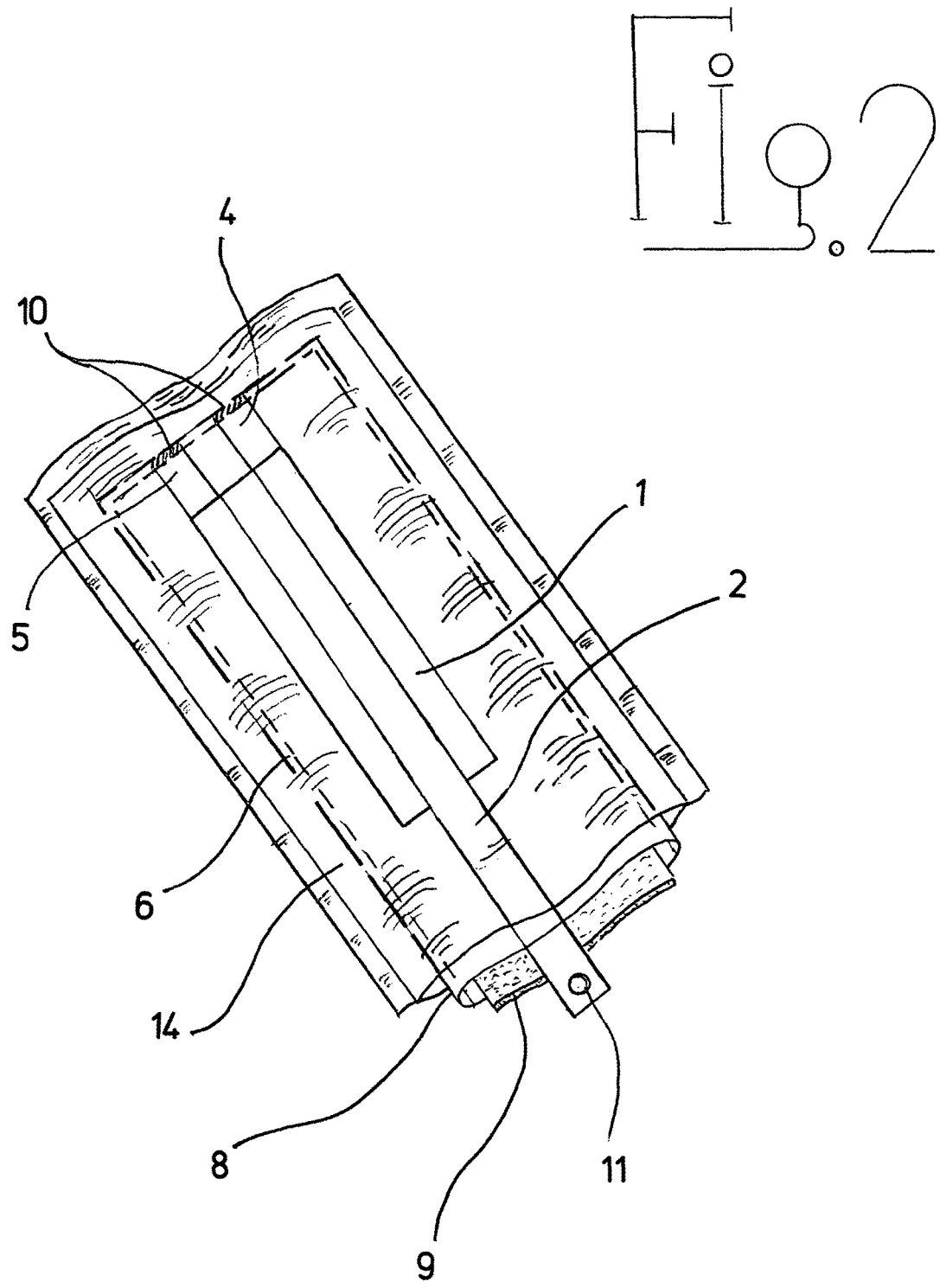
FIG. 2 is a perspective view of the outer bag opened at one end revealing its content.
Figure 3:
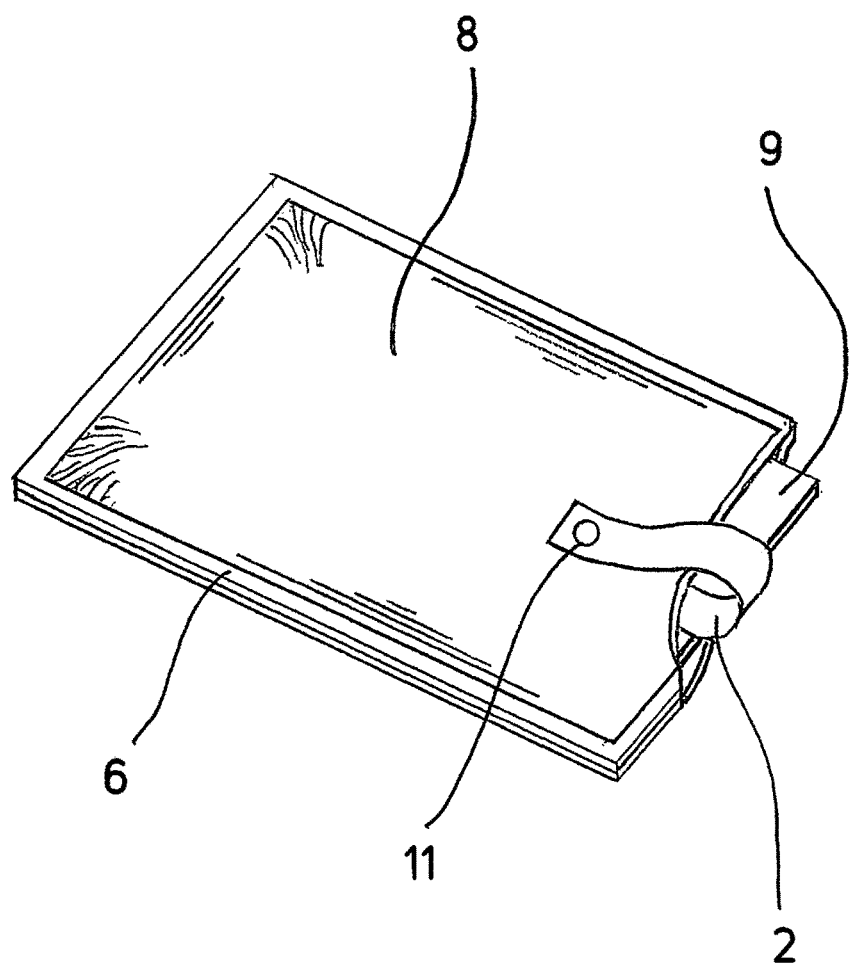
FIG. 3 is a perspective view of the protective pouch opened at one corner exposing its content.
Figure 4:
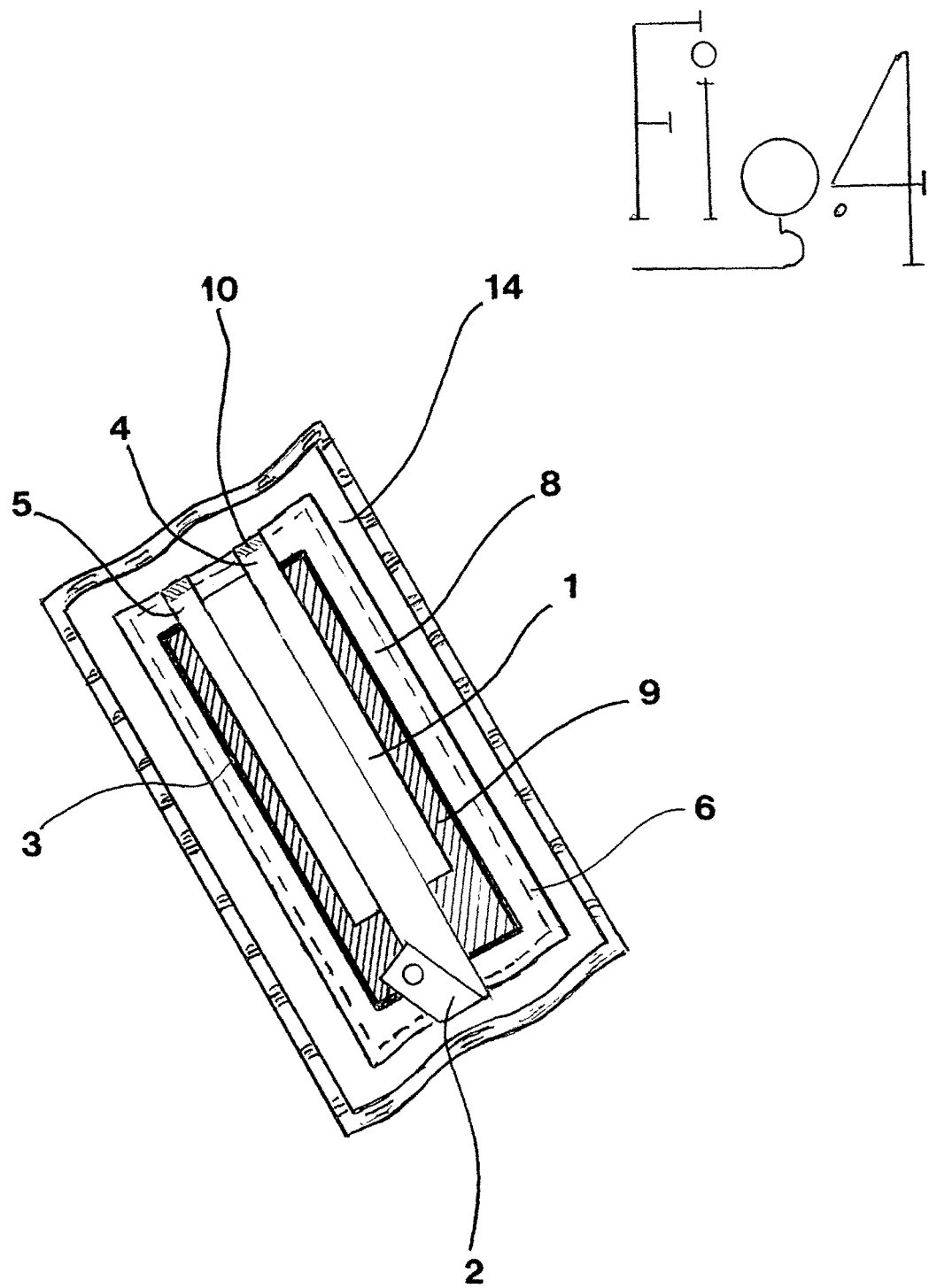
FIG. 4 is a perspective view of the outer pouch with see through of the content including the protective sleeve, splint material and the liquid pouch comprising the folded pull through extension tab.

Turning now to the drawings, in which similar reference characters denote similar elements throughout the several views, the attached figures illustrate a liquid containing pouch 1 sealed at its periphery 3 and having two short extensions tabs 4 and 5 at one end and a long extension tab 2 folded and laid on top of the pouch and pointing toward the opposite end of the pouch. The end of said long extension tab has a hole 11 to allow the operator a better hold and grab the end as seen in FIG. 1. The liquid pouch as described above is located on top or sandwiched between the layers of the casting material 9 situated inside the protective pouch 8 as shown in FIG. 2. Furthermore, protective pouch 8 is sealed all around 6 except for a small area allowing for the long extension tab 2 to pass through. Finally, the protective pouch and its contents will be packaged in a tear resistant, impermeable to water and airtight outer package 14.

In use, the operator will manually tear the outer package and will remove the protective pouch 14 containing the casting material 9 and the liquid pouch 1. At this point, there is no need for using water or other liquid since the water for hardening the cast material will be supplied by the gel inside the liquid pouch 1. As seen in FIG. 1, tearing of the liquid pouch can be easily accomplished by holding the protective pouch at one end and firmly grasping extension tab 2 at the other end of the protective pouch and pulling it out. In doing so, the liquid pouch will be torn along its middle section throughout its entire length. Subsequently, the gel will escape and come in contact with the casting material 9. Kneading the protective pouch will facilitate spreading of the water-laden gel over the entire splint material. The casting material 9 is conventionally made from fiberglass or weaved polyester impregnated with water curable resin such as polyurethane obtained from arylalkane diisocuanates and mainly from diphenylmethane diisocyanates, which will cure after been in contact with the water-laden gel and become hard allowing its use to immobilize a broken limb. It is clear that the advantage of having the water-laden gel in an impermeable pouch within a sterile protective sleeve is significant since it provides a simple self curing, clean and fast method eliminating the need for messy wet conventional technique where the cast is dipped in non-sterile water. The dry and self-curing splint of the present invention will avoid application of wet splint directly onto the patient's skin, which will cause maceration and infection.

The liquid pouch 1 as shown in FIG. 2, has two extensions tabs 4 and 5, which are secured and included in the heat weld 10 at the periphery of the protective pouch 8 so when the liquid pouch opening means 2 is pulled, the pouch will remain relatively stationary. In addition, the pouch will also be adherent to the splint material in view of the normally tacky nature of the water curable resin.

The gel used to cure the resin in the present invention can be usually supplied in rich in water gel like phase. Materials such as Propylene Glycol, Polypropylene Glycol, hydroxypropyl and hydroxymethyl cellulose as well as starch and thickeners. The amount of water needed to cure the resin and trigger the polymerization reaction is minimal. Furthermore, appropriate amounts of accelerators can be added to the water laden gel in order to facilitate and accelerate the resin curing process.

While the embodiment of the present invention as disclosed herein are considered for purpose of disclosure to be preferred, it is to be understood that this invention is intended to cover all changes and modifications in the disclosed embodiments which will fall within the scope of the invention.

What is claimed:

1. An orthopedic splint system comprising:
   a) a water curable orthopedic splint material comprising of one or more strips, each strip having a length dimension longer than a width dimension; and
   b) a liquid pouch containing water and an opening means allowing the release of the water from within the liquid pouch to come in direct fluid contact with splint material, the liquid pouch positioned adjacent to a strip of the splint material;
   c) wherein said liquid pouch provides two-extension tabs; and
   d) a protective pouch which contains at least a part of the splint material and a part of the liquid pouch.

2. The system of claim 1, wherein the liquid pouch contains water-laden gel rich in water and when the pouch is ruptured, the water-laden gel comes into fluid contact with the splint material.

3. The system of claim 2, wherein the water-laden gel contains an at least one of an accelerator, a hardener and a thickener.

4. The system of claim 1, wherein the splint material is in the form of generally flat strips.

5. The system of claim 1 wherein said opening means is an extension tab, a part of which is in contact with the liquid pouch, and a further part of which is laid over the liquid pouch, and when the extension tab is extended, extends beyond an end of the liquid pouch.

6. The system of claim 1 wherein the said opening means is an extension tab, a part of which is in contact with the liquid pouch, and an end of which extends therefrom and exits from an end of the protective sleeve.

7. The system of claim 1 which further comprises two end extension tabs extending from the liquid pouch and which are secured and anchored to an edge of the protective sleeve.

8. The system of claim 1 which further comprises
   d) a tear resistant water impermeable outer package, which at least in part encloses the protective sleeve, the splint material and the liquid pouch.

9. The system of claim 1 wherein the orthopedic splint material includes water curable polyurethane resin.

10. The system of claim 1, wherein the water is in a form of a water-laden gel comprising one or more of: propylene glycol, hydroxypropyl cellulose, hydroxymethyl cellulose, and starch.

11. The system of claim 1, wherein the protective pouch is sprayed with an antiseptic solution.

12. The system of claim 1, which comprises multiple layered strips of splint material.

13. The system of claim 12, wherein the liquid pouch is interposed between two layered strips of splint material.

14. The system of claim 1, wherein the splint material comprises fiberglass or woven polyester impregnated with a water curable resin.

15. The system of claim 14, wherein the water curable resin is a material which cures after being in contact with a water-laden gel, and becomes hard.

16. An orthopedic splint system comprising:
   a) water curable orthopedic splint material in a form of multiple layered strips having a length dimension longer than a width dimension; and
   b) a liquid pouch containing a water-laden gel positioned between the layers of the splint material; and
   c) wherein said liquid pouch provides two extension tabs; and
   wherein said liquid pouch is provided with opening means allowing the release of the water-laden gel to come in direct fluid contact with splint material.

17. The system of claim 16 wherein two end extension tabs are secured and anchored to an edge of the protective sleeve providing stability during opening of said liquid pouch.

18. The system of claim 16 wherein the orthopedic casting material is situated inside an air and watertight protective sleeve.

19. The system of claim 16 wherein the splint material includes water curable polyurethane resin.

* * * * *